United States Patent [19]

Jones

[11] Patent Number: 4,905,710
[45] Date of Patent: Mar. 6, 1990

[54] SURGICAL DRAPE

[76] Inventor: David A. Jones, 48, Eaton Crescent, Swansea, Glamorgan, SA1 4GL, United Kingdom

[21] Appl. No.: 160,858

[22] Filed: Feb. 26, 1988

[30] Foreign Application Priority Data

Feb. 28, 1987 [GB] United Kingdom ............... 8704784

[51] Int. Cl.⁴ .............................................. A61F 13/00
[52] U.S. Cl. .................................... 128/849; 128/852; 128/853
[58] Field of Search ............... 128/132 D, 132 R, 849, 128/850, 851, 852, 853, 854, 855, 856

[56] References Cited

U.S. PATENT DOCUMENTS

| 1,554,692 | 9/1925 | Shane | 128/849 |
|---|---|---|---|
| 1,724,443 | 8/1929 | Wheeler | 2/69 |
| 3,030,957 | 4/1962 | Melges | 604/357 |
| 3,236,370 | 2/1966 | Pereny et al. | 206/440 |
| 3,791,382 | 2/1974 | Collins | 128/132 D |
| 3,800,790 | 4/1974 | Collins | 128/132 D |
| 3,930,497 | 1/1976 | Krebs et al. | 128/853 |
| 3,968,792 | 7/1976 | Small | 128/132 D |
| 4,119,093 | 10/1978 | Goodman | 128/856 |
| 4,414,968 | 11/1983 | Amin | 128/132 D |
| 4,433,019 | 2/1984 | Chumbley | 428/110 |
| 4,476,860 | 10/1984 | Collins et al. | 128/132 D |
| 4,524,767 | 6/1985 | Glassman | 128/132 D |
| 4,574,796 | 3/1986 | Lundstrom et al. | 128/855 |
| 4,679,552 | 7/1987 | Caspari | 128/856 |
| 4,711,236 | 12/1987 | Glassman | 128/132 D |
| 4,730,609 | 3/1988 | McConnell | 128/132 D |
| 4,745,915 | 5/1988 | Enright et al. | 128/132 D |

FOREIGN PATENT DOCUMENTS 0191296 8/1986 European Pat. Off. .
1604033 12/1981 United Kingdom .

Primary Examiner—Robert A. Hafer
Assistant Examiner—Michael Brown
Attorney, Agent, or Firm—Young & Thompson

[57] ABSTRACT

A surgical drape for limb surgery has a main bacteria-proof flexible sheet 10, formed with a transparent operating window 15 having adhesive on its underside. Spaced from the window is an upwardly projecting pocket 18 to receive the length of the limb and between the window and the pocket is a folded area 12 which allows the mouth 20 of the pocket to be drawn away from the window to allow the distal end of the limb to be inserted.

14 Claims, 2 Drawing Sheets

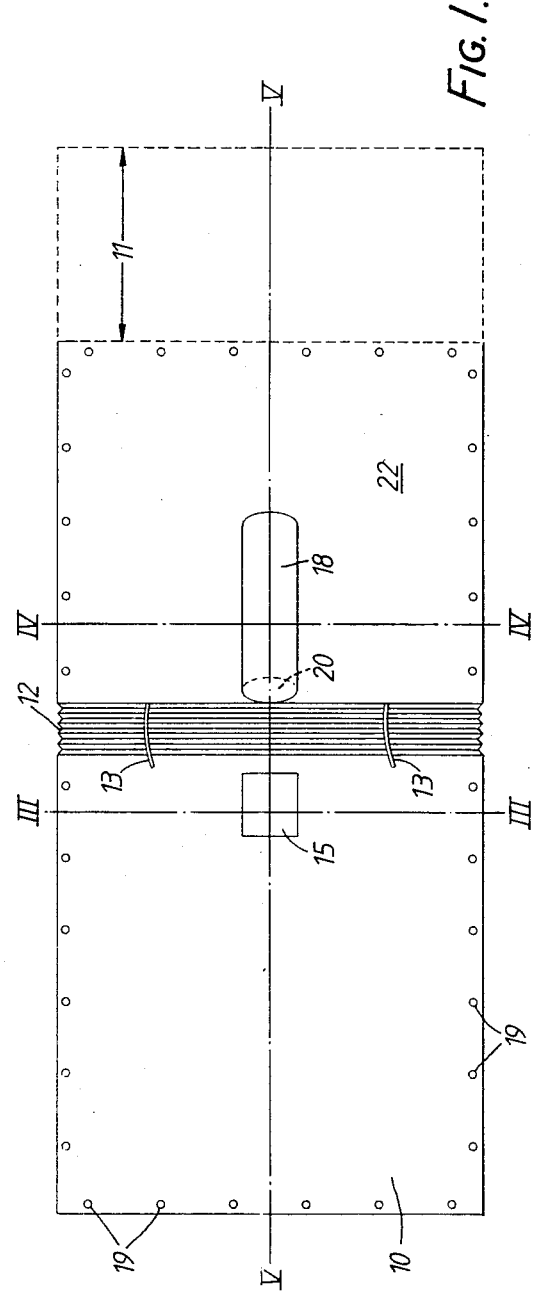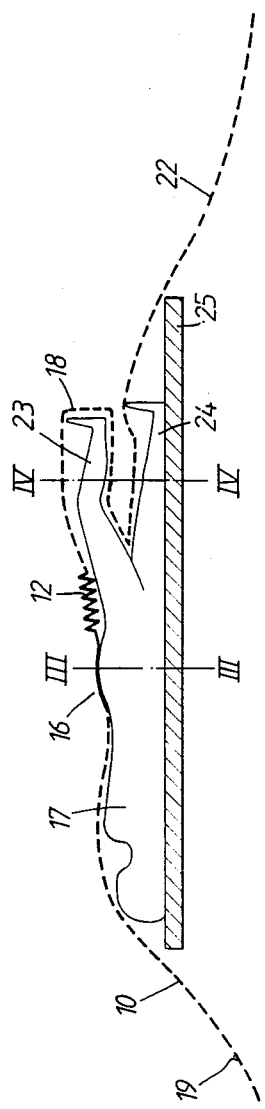

SURGICAL DRAPE

This invention relates to the design of a surgical drape that permits ease of use by the surgeon and also maintains sterility, whilst enabling the surgeon to move an adjacent limb or appendage. The invention is particularly, though not exclusively, applicable for use in surgery adjacent a limb joint, more particularly at the promixal end thereof, for example in hip joint replacement.

Current draping systems for proximal limb surgery have required the use of at least three separate parts, and it is necessary that the limb itself is separately draped. These conditions are not ideal for the maintenance of sterility.

It is an object of the present invention to provide a drape which will reduce the possibility of infection, whilst still enabling the surgeon to have access to the draped limb in such a way that he or his assistants may move that limb as required during operation, and at the same time maintain sterility.

In this description, the operation of total hip replacement is used as an example but the same principles apply to any area where part of the body and an adjacent appendage requires to be draped (and at the same time to be fully manoeuvrable within the surgical field)-whilst maintaining sterile conditions, e.g. the shoulder. It may also be employed for operations on children of all ages, and living creatures of other species, for example in veterinary surgery.

Broadly stated, the invention consists in a surgical drape for use in surgery on a limb or appendage of the body, comprising a flexible bacteria-proof sheet, having a transparent area designed to be placed over an operating site, and to be made to adhere on its reverse side to the adjacent skin, and a pocket for receiving the limb or appendage, having a mouth opening onto the reverse side of the sheet at a distance from the transparent area, and effectively closed at the other end of the pocket.

Preferably, the surgical drape has an adhesive substance applied to the reverse side of the sheet at or around the transparent area.

In such cases the drape also preferably has a readily removeable non-adherent temporary cover applied initially over the adhesive.

Alternatively, the surgical drape may be formed so that the reverse side of the sheet, at or around the transparent area, is formed and arranged to adhere to an adhesive substance applied to the skin.

So as to facilitate insertion of the limb or appendage into the pocket, the pocket mouth preferably opens onto the same side of the sheet as the side carrying the adhesive substance or the adhering surface. It will be appreciated however that initially the pocket may be turned "inside-out" so that the mouth opens onto the opposite or front side of the sheet. Then while inserting the limb into the pocket, the pocket is re-inverted.

According to a particularly preferred feature of the invention, the surgical drape is so arranged that the mouth of the pocket is moveable towards and away from the transparent area. In one particular construction for this purpose, part of the sheet between the transparent area and the mouth of the pocket is folded or foldable to allow adjustment in the spacing. In such cases, the surgical drape may include means for holding the two main parts of the drape in adjacent positions while the intervening portion is folded.

It will be appreciated that the position of the pocket should be such that the distal end of the limb or appendage can be inserted into the pocket without difficulty. Thus, preferably the mouth of the pocket is, or can be, displaced from the transparent area by a distance greater than half the length of the pocket. The length of the pocket and the distance aforesaid will depend upon the size and length of the limb, but in the case of a leg the mouth of the pocket is preferably spaced from the transparent area by a distance of at least 0.75 m. It will be appreciated that a surgical drape designed for surgery on a smaller limb, such as a finger, will require a surgical drape of different dimensions, with a smaller spacing between the pocket and transparent area. In any case, the surgical drape preferably includes means for retaining the limb or appendage within the pocket.

From another aspect, the invention consists in a surgical drape as defined having a pocket or receptacle on the front side of the drape arranged to receive blood from the operation wound, and means for discharging or collecting blood from the receptacle. There may be means on the front side of the sheet for holding or locating surgical instruments or the like.

The invention may be performed in various ways and one specific embodiment with a number of possible modifications will now be described by way of example with reference to the accompanying drawings, in which:

FIG. 1 is a diagrammatic plan view of a surgical drape according to the invention, FIG. 2 is a diagrammatic side elevation partly in section showing the drape in position for an operation.

Figure 3:
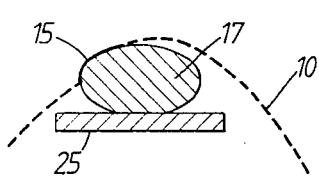
FIG. 3 is a diagrammatic cross-section on the line III—III in FIGS. 1 and 2.
Figure 4:
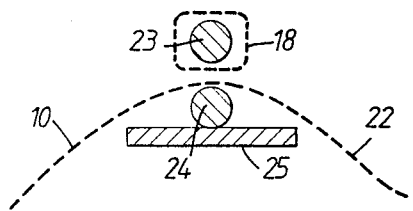
FIG. 4 is a diagrammatic cross-section on the line IV—IV in FIGS. 1 and 2.
Figure 5:
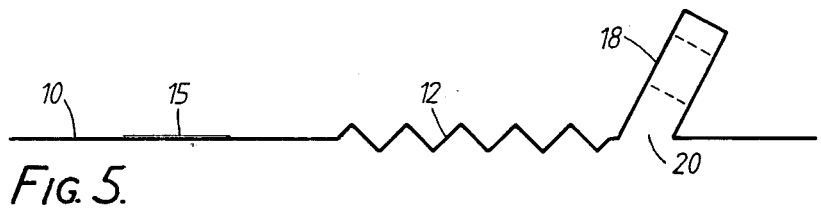
Figure 6:
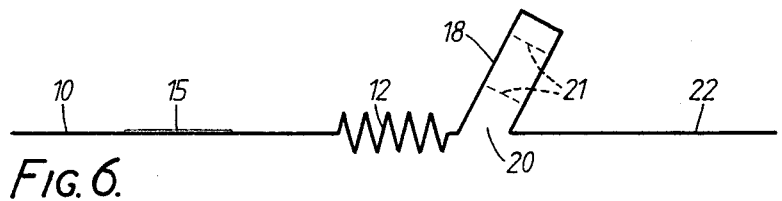
Figure 7:
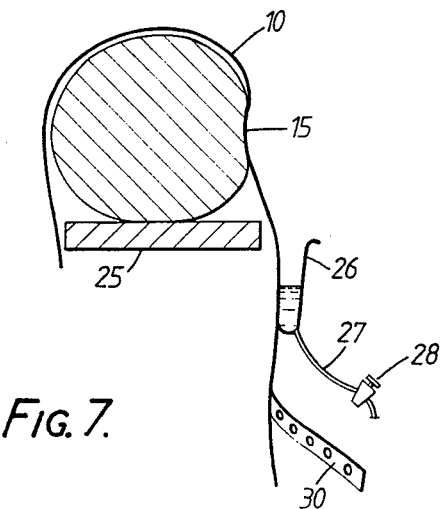

FIG. 5 is a diagrammatic cross-section on the line V—V in FIG. 1 illustrating the drape in its expanded position with the pocket moved away from the operating window, FIG. 6 is a diagrammatic view corresponding to FIG. 5 showing the drape contracted to move the pocket closer to the window, and FIG. 7 is a further diagrammatic crosssection similar to that of FIG. 3 illustrating certain possible modifications.

In the first example the drape comprises a generally rectangular flexible sheet 10 formed of a bacteria-proof material, for example a synthetic plastics material such as heavy duty polythene, or an impregnated paper. The material may be dual or multiply incorporating several layers, and may include or consists of a thermal insulating layer. Preferably it is colored or opaque, but in some cases it may be transparent. The overall size for use in hip surgery in an adult will normally be approximately 3.5×1.5 meters. However, for reasons to be explained, it is desirable that the drape can be expanded lengthwise by distance of approximately 0.7 meters, as indicated at 11 in FIG. 1, and for this purpose the drape may be initially folded transversely at 12 into a number of plications or pleats. The drape may be held in its contracted form by means of a pair of detachable or elastic straps 13.

At the intended site of the operation (in this case hip replacement) the drape is provided with a small rectangular "window" 15 of a transparent bacteria-proof material, which is effectively and permanently bonded or united with the main area of the drape. This window panel is coated with a suitable strong adhesive on its undersurface, to be applied to the patient's skin, which has previously been thoroughly cleaned. The adhesive is initially protected by a removable layer of, for example, wax paper which can be simply peeled off to allow this window to be applied to the skin.

The drape is formed also with a projecting pocket or envelope 18 which in the case of hip replacement is suitably dimensioned to receive the patient's leg extending substantially the full length from the foot to the hip joint. In this example accordingly the pocket 18 may be approximately 1.5 meters in length and have a diameter of approximately 0.3 meters. The pocket is preferably provided with means for retaining the limb or appendage within the pocket or for locating the pocket over the limb after insertion. For example, the pocket may be provided with internal or external tie strings 21 or drawstrings, or may be elasticated, i.e. having one or more external elasticated hoops to surround the limb. The surgical drape is prepacked initially in a steralised sealed package, preferably with the adhesive panel uppermost or readily accessible, and the remainder of the drape carefully folded so that after this adhesive panel has been placed in position on the operation site 16 the remainder of the drape can be easily opened out to cover the body 17, including the upper and lower legs 23,24 without interfering with the sterility. Weights 19 around the edge of the drape hold the periphery below the level of the operating table 25. After the window 15 has been made to adhere to the skin adjacent the hip joint the straps 13 are freed and the lower part of the drape is drawn downwards to open out the folds 12, as illustrated in FIG. 5. In this position the mouth 20 of the pocket 18 is spaced by a distance of approximately 1.5 meters from the window. It is therefore possible to insert the distal end (i.e. the foot) of the limb in question into the pocket after which the plications or folds 12 are again restored, as shown in FIG. 6, so that the mouth 20 of the pocket moves closer to the window 15 until substantially the whole length of the leg is enveloped in the pocket. The elasticated hoops or drawstrings 21 are tightened or allowed to tighten to hold the pocket in position. The lower part 22 of the main drape is placed over the other leg of the patient and the edges of the drape are allowed to fall below the level of the operating table 25.

FIG. 7 illustrates a possible modification in which the drape is provided with a catchment receptacle or bag 26 in such a position that it will be located adjacent to but below the level of the window 15 when applied to the operating site on the patient; thus any blood from the operating wound will drain into the bag and can be withdrawn through a conduit 27 and control valve 28 into a receptacle, not illustrated, where the blood may be treated as required and ultimately returned by infusion to the patient. In FIG. 7 the drape is also shown with an added projecting strap 30 formed with holes or slits to receive and locate surgical instruments or the like which may be needed by the surgeon close to hand. In the example described the transparent window 15 has an overall layer of adhesive on its underside, but it may be sufficient to apply the adhesive only round a limited area of the window. In a possible alternative there is no adhesive initially applied to the window itself, but the adhesive is applied at the start of the operation to the skin of the patient, for example by spraying or painting. In such case the window must be formed of a material capable of making a rapid and effective bond with the adhesive.

It will be understood that for purposes of sterility it is vital that the upper or surgeon's side of the drape should be separated from the lower patient's side. Preferably the whole drape including the window and the pocket are formed as one integral or inseparable unit. In some examples, however, components may be formed separately and later bonded or united, with particular attention paid to preserving the bacteria seal. In the example described the pocket 18 initially projects upwards on the surgeon's side and the mouth 20 opens downwards to allow the limb to be introduced. It will be understood, however, that if such a pocket is turned inside out temporarily before the operation its mouth will open onto the surgeon's side, though the sterile seal will be maintained. In this inverted position it may be more easy to apply the temporary connectors holding the pocket in position on the limb before the pocket is re-inverted into its intended position.

I claim:

1. A surgical drape for use in surgery on a part of a body adjacent to an appendage of the body, comprising a flexible bacteria-proof sheet, having a transparent window designed to be placed over an operating site and to be made to adhere on its reverse side to the adjacent skin, a pocket forming a continuous part of the drape for receiving the appendage, and a pleated portion between the window and the pocket, the pocket having a mouth sealed to the drape around its lip and opening onto the reverse side of the sheet at a distance from the transparent area, and effectively closed at the other end of the pocket, the drape being so constructed and arranged that the mouth of the pocket is movable towards and away from the window by manipulation of said pleated portion of the drape.

2. A surgical drape according to claim 1, having an adhesive substance applied to the reverse side of the sheet adjacent the window.

3. A surgical drape according to claim 2, having a readily removable non-adherent temporary cover applied initially over the adhesive.

4. A surgical drape according to claim 2, in which the pocket mouth opens onto the same side of the sheet as the side carrying the adhesive substance.

5. A surgical drape according to claim 1, in which the reverse side of the sheet, adjacent the window, is formed and arranged to adhere to an adhesive substance applied to the skin.

6. A surgical drape according to claim 1 having two main parts respectively located on opposite sides of said pleated portion, and including means for holding the two main parts of the drape in adjacent positions to hold the pleated portion folded.

7. A surgical drape according to claim 1, in which the mouth of the pocket is displaced from the transparent area by a distance greater than half the length of the pocket, when said pleated portion of the sheet is distended.

8. A surgical drape according to claim 1, in which the mouth of the pocket is spaced from the transparent area by a distance of at least 0.75 m, when said pleated portion of the sheet is distended.

9. A surgical drape according to claim 1, including means for retaining the appendage within the pocket.

10. A surgical drape according to claim 1, including means on the front side of the sheet for locating surgical instruments.

11. A surgical drape according to claim 1, incorporating at least one weight adjacent the periphery of the drape, to assist in holding the drape in position.

12. A surgical drape according to claim 1, in which the sheet, window, and pocket are formed as one inseparable unit.

13. A surgical drape according to claim 17, including a receptacle on the front side of the drape arranged to receive fluids which may pass from the operation wound through an incision in the window, and means for discharging fluids from the receptacle.

14. A surgical drape according to claim 1, wherein the pocket has a mouth sealed to the drape around its lip and opening onto the reverse side of the sheet at a distance from the transparent area, and effectively closed at the other end of the pocket, and including means for retaining the appendage in position within the pocket.

* * * * *